United States Patent [19]

Bruzzese et al.

[11] 4,279,926
[45] Jul. 21, 1981

[54] METHOD OF RELIEVING PAIN AND TREATING INFLAMMATORY CONDITIONS IN WARM-BLOODED ANIMALS

[75] Inventors: Tiberio Bruzzese, Milan, Italy; Rodolfo Ferrari, deceased, late of Milan, Italy, by Lorenzo Ferrari, executor

[73] Assignee: SPA-Societa Prodotti Antibiotici S.p.A., Italy

[21] Appl. No.: 63,553

[22] Filed: Aug. 3, 1979

Related U.S. Application Data

[63] Continuation-in-part of Ser. No. 956,531, Oct. 16, 1978, abandoned, which is a continuation of Ser. No. 556,413, Mar. 7, 1975, abandoned.

[30] Foreign Application Priority Data

Mar. 7, 1974 [GB] United Kingdom ............... 10239/74

[51] Int. Cl.³ .................. A61K 31/205; C07C 101/24
[52] U.S. Cl. ................................. 424/316; 260/501.11
[58] Field of Search ..................... 260/501.11; 424/316

[56] References Cited

U.S. PATENT DOCUMENTS

| 3,624,142 | 11/1971 | Shen | 260/501.11 |
|---|---|---|---|
| 3,686,183 | 8/1972 | Depon | 260/501.11 |
| 3,821,289 | 6/1974 | Diamond | 260/501.11 |
| 3,931,302 | 1/1976 | Allais et al. | 260/501.11 |
| 4,001,301 | 1/1977 | Fried et al. | 260/501.11 |

FOREIGN PATENT DOCUMENTS

| 2316802 | 10/1973 | Fed. Rep. of Germany | 260/501.11 |
|---|---|---|---|
| 2419317 | 9/1975 | Fed. Rep. of Germany | 260/501.11 |
| 2508895 | 9/1975 | Fed. Rep. of Germany | 560/501.11 |
| 2711964 | 9/1978 | Fed. Rep. of Germany | 424/316 |
| 385222 | 4/1973 | Spain | 260/501.11 |
| 971700 | 9/1964 | United Kingdom | 260/501.11 |

OTHER PUBLICATIONS

Chemical Abstracts, 76, 6721(b), 1972.

*Primary Examiner*—G. T. Breitenstein
*Attorney, Agent, or Firm*—Wenderoth, Lind & Ponack

[57] ABSTRACT

The present invention provides a method of relieving pain and of treating inflammatory conditions in warm-blooded animals, including humans, which comprises administering to a warm-blooded animal suffering from an inflammatory condition a phenyl-alkanoic acid salt of the general formula:

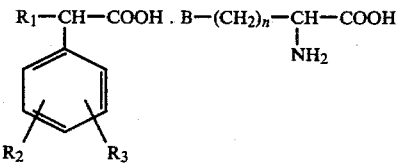

wherein $R_1$ is a hydrogen atom or a methyl radical, $R_2$ is a halogen atom or an alkyl radical containing up to 5 carbon atoms, which may be straight-chained or branched, for example an isobutyl radical, or is a cyclohexyl radical or is a phenoxy or benzoyl radical, which may be substituted by one or two halogen atoms, $R_3$ is a hydrogen atom or an allyloxy radical or $R_2$ and $R_3$, together with the phenyl nucleus to which they are attached, represent a naphthyl ring system containing a methoxy substituent, B is a primary, secondary or tertiary amino group or a guanidino or amidino group and n is a whole number not greater than 5, for example B is an amino group and n is 3 (ornithine), B is an amino group and n is 4 (lysine) or B is a guanidino radical and n is 3 (arginine).

14 Claims, 3 Drawing Figures

METHOD OF RELIEVING PAIN AND TREATING INFLAMMATORY CONDITIONS IN WARM-BLOODED ANIMALS

This is a continuation-in-part of Ser. No. 956,531, filed Oct. 16, 1978, now abandoned which in turn is a continuation of Ser. No. 556,413, filed Mar. 7, 1975, now abandoned.

BACKGROUND OF THE INVENTION

Certain phenyl-alkanoic acids are known from the literature and some of them are said to possess valuable pharmacological activities, for example, an analgesic, anti-inflammatory or anti-pyretic action, whereas others are used clinically, for example, in the treatment of rheumatoid arthritis.

However, these known phenyl-alkanoic acids suffer from certain disadvantages, due essentially to their insolubility in water, to their acidity and, to a certain extent, to their toxicity. Thus, their insolubility restricts their possibilities for use; for example, they cannot be administered parenterally as injections or orally as drops, i.e. by methods which are especially suitable in early infancy and adolescence, and, at the same time, it limits their availability to the living organism after oral administration and results in a relatively low, incomplete and non-uniform absorption.

Furthermore, the acidity of the known phenyl-alkanoic acids often induces intolerance effects and may even give rise to ulceration of the gastro-intestinal mucosa, with the risk of severe haemorrhages in patients with a predisposition thereto.

It is also known that a number of other acidic anti-inflammatory substances, for example aspirin, phenylbutazone, the derivatives of mefenamic acid and indomethacine, also show these undesired side-effects in an even more pronounced form.

The acute toxicity of the phenyl-alkanoic acids appears to be very low both in pharmacological use and in clinical use for humans, although an occasional increase in serum transaminases, the appearance of jaundice and other secondary effects, even though very rare, suggest the possibility, with some derivatives in this series, of hepatic damage which would induce a certain degree of caution in the prolonged treatment of patients who initially suffered from hepatic dysfunction.

We have now found that the important disadvantages of the phenyl-alkanoic acids could be substantially avoided by means of salification with basic amino acids, the salts thus obtained being stable and extremely soluble in water to give substantially neutral aqueous solutions.

Other salts which we initially considered were those with the alkali metals. These are also soluble in water but proved to be less suitable for therapeutic use due to their strongly basic pH and, in particular, because the high dosage level needed resulted in considerable amounts of the alkali metals also being administered, which are frequently contraindicated.

SUMMARY OF THE INVENTION

Thus, the present invention provides a method of relieving pain and of treating inflammatory conditions in warm-blooded animals, including humans, which comprises administering to a warm-blooded animal suffering from pain or from an inflammatory condition a phenyl-alkanoic acid salt of the general formula:

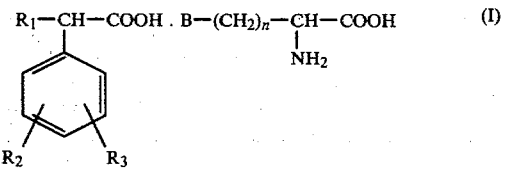

wherein $R_1$ is a hydrogen atom or a methyl radical, $R_2$ is a halogen atom or an alkyl radical containing up to 5 carbon atoms, which may be straight-chained or branched, for example an isobutyl radical, or is a cyclohexyl radical or is a phenoxy or benzoyl radical, which may be substituted by one or two halogen atoms, $R_3$ is a hydrogen atom or an allyloxy radical or $R_2$ and $R_3$, together with the phenyl nucleus to which they are attached, represent a naphthyl ring system containing a methoxy substituent, B is a primary, secondary or tertiary amino group or a guanidino or amidino group and n is a whole number not greater than 5, for example B is an amino group and n is 3 (ornithine), B is an amino group and n is 4 (lysine) or B is a guanidino radical and n is 3 (arginine).

DETAILED DESCRIPTION OF THE INVENTION

Figure 1:
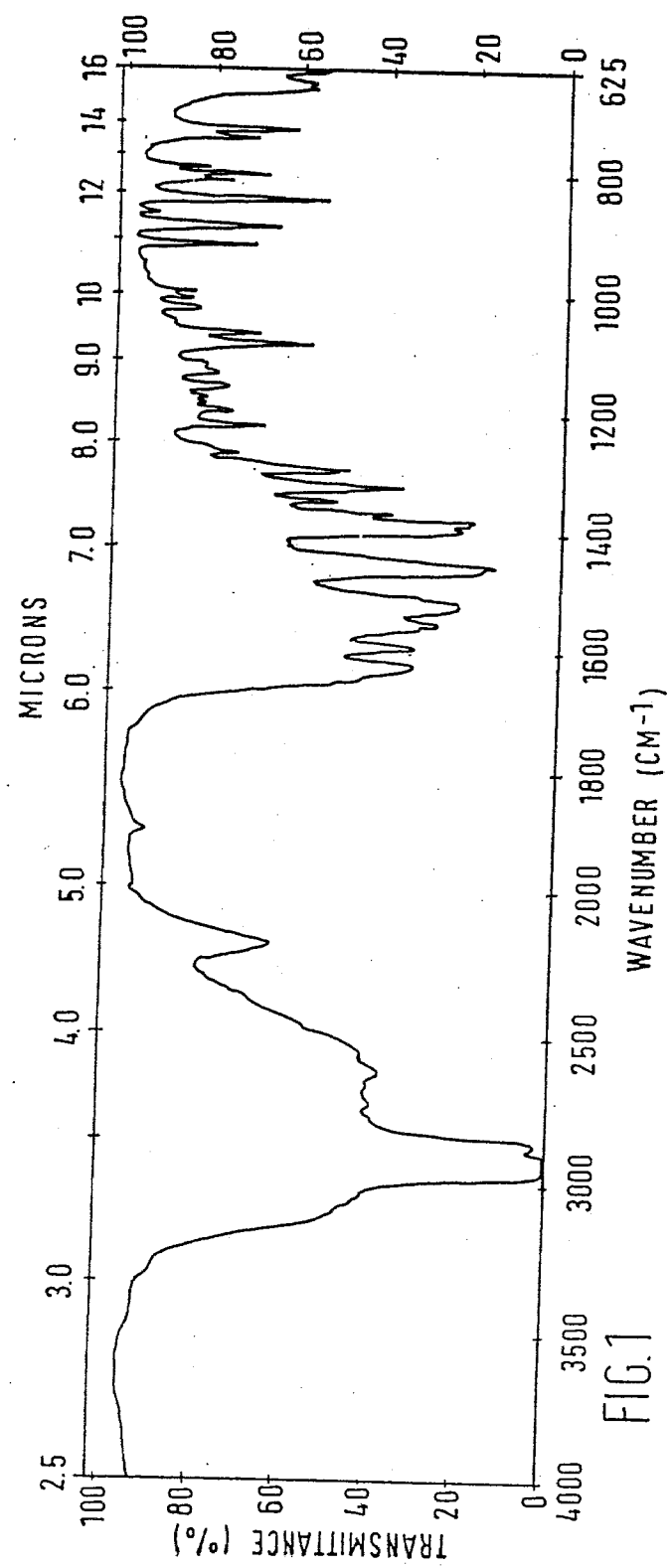

Typical examples of the salts (I) to be used according to the present invention include the 2-(4-isobutyl-phenyl)-propionate of lysine and the 2-(4-isobutyl-phenyl)-propionate of arginine, i.e. salts derived from 2(4-isobutyl-phenyl)-propionic acid (ibuprofen) and two naturally-occurring basic amino acids.

The phenyl-alkanoic acids used for the preparation of the salts (I) are known from the literature.

An important characteristic of the salts to be used according to the present invention is their extremely high degree of solubility in water, which, in some cases, is more than 40–50%, so that they can be administered by injection in all those cases requiring quick and effective action, especially as analgesics, i.e. for the relief of pain, or when direct intervention is needed, for example, in cases of emergency, where very high fever, delirium or loss of consciousness, make other methods of administration, which act too slowly, ineffective or impossible. However, this does not preclude the oral administration of the salts (I): on the contrary, the solubility of the salts (I) permits their better use, both from a technical and pharmaceutical standpoint, for the production of preparations to be administered orally in drop form with consequently improved blood levels and increased efficiency.

As an illustration of the action of the salts (I), experimental results are given in the following Tables of some pharmacological tests carried out with the lysine salt of 2-(4-isobutyl-phenyl)-propionic acid. In order to determine the anti-inflammatory and analgesic action, male Wistar rats weighing from 90–110 g. were injected subplanatarly with 0.2 ml. of a 1% carragheen solution and, after 1 hour, with the test substance. At intervals after the treatment, the size of the treated paw and its sensitivity to pain under pressure were evaluated. Tables 1, 2 and 3 show that the lysine salt of 2-(4-isobutyl-phenyl)-propionic acid is, when administered orally, as active as or more active than the equivalent dose of the corresponding free acid and is as effective as a double dose of phenyl-butazone.

TABLE 1

| Active compound | Dose mg./kg. p.o. | Variation in size of the inflamed paw (%) Length of treatment | | Variation in threshold of pain in the inflamed paw (%) Length of treatment | |
|---|---|---|---|---|---|
| | | 3 hours | 5 hours | 3 hours | 5 hours |
| Phenyl-butazone | 100 | −12.3 | −16.7 | +104.8 | +65.6 |
| 2-(4-isobutyl-phenyl)-propionic acid | 50 | −13.3 | −13.9 | +79.0 | +54.1 |
| lysine salt of 2-(4-isobutyl-phenyl)-propionic acid | 50* | −17.3 | −17.8 | +101.6 | +62.3 |

*Expressed as active substance.

TABLE 2

| Expt. No. | Active material | route | dose mg/kg | Number of animals | Paw volume in ml. - carrageenin oedema (% variation referred to control) | | | | |
|---|---|---|---|---|---|---|---|---|---|
| | | | | | 0 hrs. | 1 hr. | 3 hrs. | 4 hrs. | 5 hrs. |
| 1 | control | — | — | 15 | 1.16 ± 0.02 | 1.45 ± 0.03 | 2.21 ± 0.06 | 2.29 ± 0.05 | 2.36 ± 0.06 |
| 2 | phenyl butazone | p.o. | 100 | 15 | 1.18 ± 0.02 | 1.54 ± 0.04 | 1.65 ± 0.05** (−25.4) | 1.75 ± 0.05** (−23.6) | 1.84 ± 0.05** (−22.0) |
| 3 | Ibuprofen | p.o. | 200 | 15 | 1.17 ± 0.02 | 1.56 ± 0.03 | 1.59 ± 0.04** (−28.5) | 1.68 ± 0.04** (−26.6) | 1.73 ± 0.04** (−26.7) |
| 4 | Ibuprofen | p.o. | 100 | 15 | 1.18 ± 0.04 | 1.55 ± 0.05 | 1.60 ± 0.06** (−27.6) | 1.75 ± 0.07** (−23.6) | 1.88 ± 0.08** (−20.3) |
| 5 | Ibuprofen | p.o. | 50 | 15 | 1.10 ± 0.05 | 1.48 ± 0.03 | 1.52 ± 0.05** (−31.2) | 1.69 ± 0.06** (−26.2) | 1.84 ± 0.07** (−22.0) |
| 6 | lysine salt of 2-(4-iso-butylphenyl)-propionic acid | p.o. | 200 (120*) | 15 | 1.12 ± 0.01 | 1.54 ± 0.03 | 1.56 ± 0.03** (−29.4) | 1.67 ± 0.05** (−27.1) | 1.77 ± 0.05** (−25.0) |
| 7 | lysine salt of 2-(4-iso-butylphenyl)-propionic acid | p.o. | 100 (60*) | 15 | 1.15 ± 0.02 | 1.63 ± 0.03 | 1.74 ± 0.05** (−21.3) | 1.88 ± 0.06** (−17.9) | 1.96 ± 0.05** (−16.9) |
| 8 | lysine salt of 2-(4-iso-butylphenyl)-propionic acid | p.o. | 50 (30*) | 15 | 1.17 ± 0.03 | 1.61 ± 0.03 | 1.79 ± 0.07 (−19.0) | 1.95 ± 0.07 (−14.8) | 2.07 ± 0.08** (−12.3) | significance of difference between treated group and control: **p = 0.01
*Expressed as active substance.

TABLE 3

| Expt. No. | Active material | route | dose mg./kg. | Number of animals | pain threshold in g. - carageenin oedema (% variation referred to control) | | |
|---|---|---|---|---|---|---|---|
| | | | | | 0 hrs. | 3 hrs. | 5 hrs. |
| 1 | control | — | — | 15 | 101.7 ± 3.19 | 52.7 ± 2.00 | 51.3 ± 2.15 |
| 2 | Fenilbutazone | p.o. | 100 | 15 | 105.3 ± 3.03 | 122.7 ± 2.92** (+132.8) | 83.7 ± 4.04** (+63.1) |
| 3 | Ibuprofen | p.o. | 200 | 15 | 101.0 ± 3.21 | 119.7 ± 3.50** (+127.1) | 85.7 ± 4.70** (+67.0) |
| 41 | Ibuprofen | p.o. | 100 | 15 | 105.3 ± 3.10 | 104.3 ± 3.51** (+97.9) | 80.3 ± 5.66** (+56.5) |
| 5 | Ibuprofen | p.o. | 50 | 15 | 101.0 ± 2.85 | 85.7 ± 4.05** (+62.6) | 70.7 ± 3.45** (+39.8) |
| 6 | lysine salt of 2-(4-isobutyl-phenyl)-propionic acid | p.o. | 200 (120*) | 15 | 97.0 ± 3.00 | 131.0 ± 5.55** (+148.6) | 83.3 ± 5.36** (+62.4) |
| 7 | lysine salt of 2-(4-isobutyl-phenyl)-propionic acid | p.o. | 100 (60*) | 15 | 108.7 ± 4.48 | 105.3 ± 4.21** (+99.8) | 78.3 ± 3.77** (+52.6) |
| 8 | lysine salt of 2-(4-isobutyl-phenyl)-propionic acid | p.o. | 50 (30*) | 15 | 101.3 ± 2.10 | 89.3 ± 6.25** (+69.4) | 67.7 ± 4.80** (+32.0) |

*Expressed as active substance
Significance of difference between treated group and control: **p = 0.01

It can be seen from the following Table 4 that it is advantageous to use intravenous administration since the lysine salt of 2-(4-isobutyl-phenyl)-propionic acid is found to be clearly more active and quicker acting than both the free acid and phenyl-butazone, even though used in doses of the order of 10 times less.

TABLE 4

| Active compound | Dose mg./kg. | Variation in threshold of pain in the inflamed paw Length of treatment | |
|---|---|---|---|
| | | 0.5 hours | 1 hour |
| Phenyl-butazone | 100 (p.o.) | +62.7 | +70.8 |
| 2-(4-isobutyl-phenyl)-propionic acid | 100 (p.o.) | +55.9 | +58.5 |
| lysine salt of 2-(4-isobutyl-phenyl)-propionic acid | 50 (p.o.) | +54.2 | +55.4 |
| | 10 (i.v.)* | +118.6 | +58.5 |

TABLE 4-continued

| Active compound | Dose mg./kg. | Variation in threshold of pain in the inflamed paw Length of treatment | |
|---|---|---|---|
| | | 0.5 hours | 1 hour |
| propionic acid | 5 (i.v.)* | +72.9 | +38.5 |

*Expressed as active substance.

From a general point of view, another important characteristic of the salts (I) is that aqueous solutions thereof are substantially neutral and are scarcely influenced by the concentration, thus making them suitable for parenteral administration.

Furthermore, the salts (I) do not contain metallic ions which might possibly impair the blood electrolytic picture and they have the advantage over conventional salts of only introducing bases which are essential for the metabolism; indeed, amino acids, such as lysine and arginine, are constituents of most proteins and, as such, they can be regarded as being physiological substances. We have also found that the use of the salts (I) considerably reduces the incidence of cases of gastric intolerance, probably due to the neutralisation of the acidity of the phenyl-alkanoic acid, and, in addition, there is a significant reduction in the number of cases of ulcerous lesions. The improved tolerance, which was to be expected in the case of parenteral administration, is also confirmed in oral use and there is the additional advantage of reduced dosage levels due to the better availability to the living organism of the water-soluble salts. In the case of the arginine salts, yet another advantage is provided: as is known, arginine is an essential substance in the metabolic cycle of nitrogenous substances, which leads to the formation and excretion of urea, and it has, therefore, been used therapeutically in cases of hyperammoniaemia, toxic states of various types and hepatic insufficiency in general. Its hepato-protective action is especially useful, therefore, in preventing or correcting any hepato-toxic effect which might be co-related to the prolonged administration of phenyl-alkanoic acids.

The salts (I) to be used according to the present invention are preferably prepared by direct salification between an appropriate phenyl-alkanoic acid, for example 2-(4-isobutyl-phenyl)-propionic acid, and an appropriate basic amino acid, for example lysine or arginine. However, it is also possible to employ double decomposition, for example, the reaction of a salt, such as sodium salt, of an appropriate phenyl-alkanoic acid and a salt, such as the hydrochloride, of an appropriate amino acid, preferably using a medium which has a low water content in order to facilitate precipitation of the sodium chloride formed by the reaction so that it can be removed by filtration.

Whatever method of preparation is employed, we have found that the reaction often gives better results if the racemic (DL) form of the amino acid is used, rather than the natural laevo (L) form which can be obtained from hydrolised protein. The products thus obtained are crystalline and can be easily worked up, generally in comparatively high yields, whereas the corresponding salts of the L-amino acid may even prove to be pasty and not easily crystallisable. However, where the optical activity of the salts (I) is not important for the purposes of the present invention, these will be designated, for convenience of expression, without any indication of the optical isomerism and D or L spatial arrangement.

The direct salification is often carried out in a medium which is predominantly aqueous, at moderate temperatures around ambient temperature, and for periods of the order of 1 or 2 hours.

The acid, which is insoluble in an aqueous medium, is added to a solution or partial suspension of the basic amino acid in a stoichiometric amount and gradually goes into solution as the salification proceeds. Finally, the product can be isolated by, for example, lyophilisation or precipitation with appropriate solvents. More often, the preparation is carried out in the presence of an excess of an organic solvent, for example of a $C_1$-$C_4$ alcohol or acetone, and, in this case, the salt precipitates or crystallises directly from the aqueous-alcoholic or aqueous-acetone medium. In all cases, very high yields are obtained.

The salts (I) are colourless substances which are soluble in water but are insoluble in acetone, diethyl ether, benzene and the like and exhibit a varying degree of solubility in alcohols.

The salts (I) to be used according to the present invention can be used in a wide variety of pharmaceutical formulations for oral and parenteral administration, by admixture with solid, liquid or semi-liquid pharmaceutical diluents or carriers. Examples of such compositions include tablets, effervescent tablets, dragees, capsules, powders, aqueous solutions and syrups for oral administration, as well as suppositories, injection solutions and ointments or tinctures for topical use, which are convenient in cases of local inflammation. In all cases, the salts (I) are diluted with an appropriate amount of a pharmaceutically acceptable solid or liquid vehicle, optionally in association with other active materials, for example antibiotics.

The following Examples illustrate the preparation of some of the salts (I) used according to the present invention:

EXAMPLE 1

74 g. 2-(4-isobutyl-phenyl)-propionic acid are dissolved in 700 ml. ethanol, whereafter a solution consisting of 105 g. of a 50% aqueous solution of D,L-lysine (equivalent to 52.5 g. of the amino acid) and 500 ml. ethanol is added dropwise. As the reaction proceeds, a copious precipitate is formed. The reaction mixture is stirred for a further hour at ambient temperature and then for 2 hours in a refrigerator, whereafter the suspended product is filtered off, washed with a little ethanol and dried in a vacuum. There are obtained about 116 g. of the D,L-lysine salt of 2-(4-isobutyl-phenyl)-propionic acid in the form of a colourless, crystalline substance with a melting point of 176°-177° C.

The product obtained in this way is substantially pure and requires no further purification, having titres of acid and base higher than 99.5%.

The infra-red spectrum (see FIG. 1 of the accompanying drawings), which is without the stretching vibration of the carboxylic C=O present in the starting acid at about 1710 cm$^{-1}$, and the physico-chemical characteristics of the product confirm its saline nature. It has a solubility in water of the order of 40%, is stable and has a substantially neutral pH.

EXAMPLE 2

Figure 2:
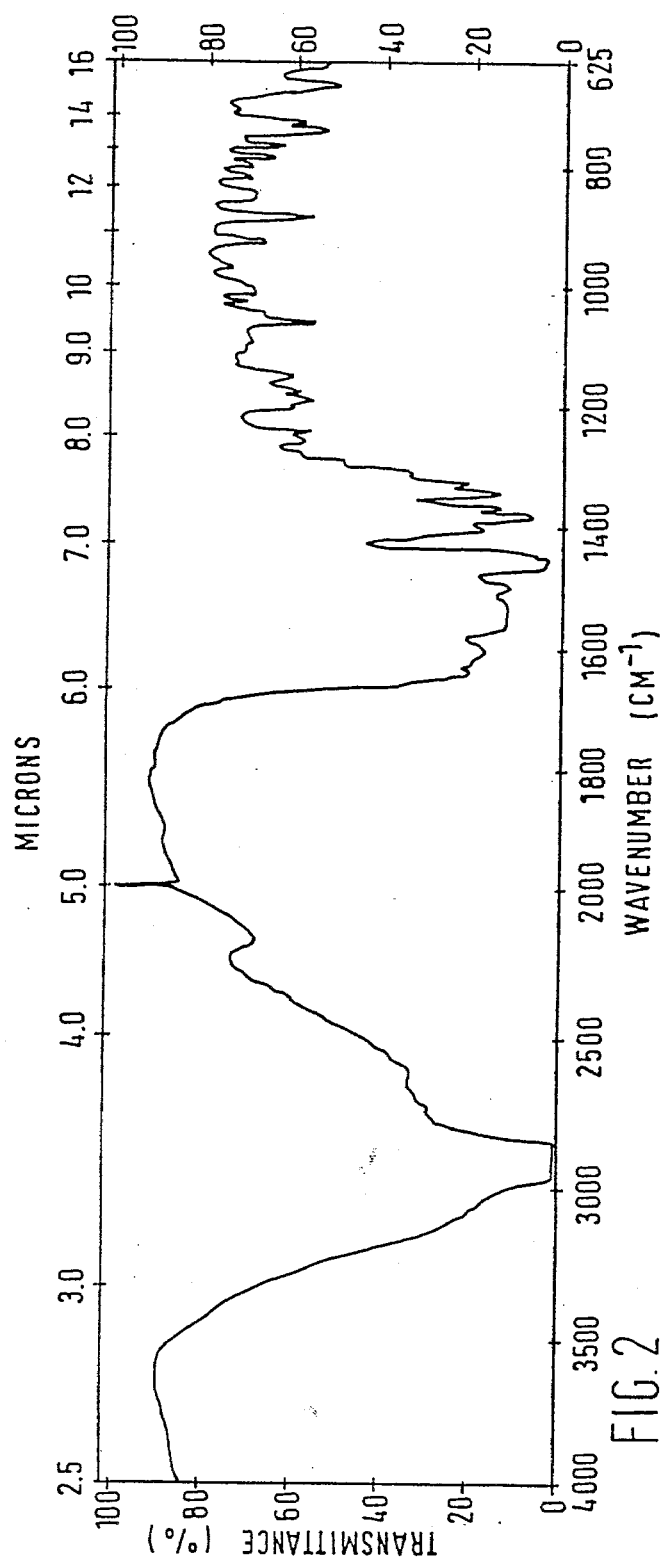

2-(4-Isobutyl-phenyl)-propionic acid is reacted with L-lysine in a manner analogous to that described in Example 1. The reaction proceeds as described in Example 1 to give the L-lysine salt of 2-(4-isobutylphenyl)-propionic acid which has the same solubility properties, stability and pH as the product obtained in Example 1; m.p. 150°–158° C.; $[\alpha]_D^{20} = +13.1°$. The IR spectrum (see FIG. 2) confirms the structure of the salt.

EXAMPLE 3

A solution of 5.1 g. lysine in 50 ml. distilled water is mixed portionwise with 8 g. 2-(4-isobutyl-phenyl)-propionic acid and the reaction mixture is then stirred, complete solution being obtained, with neutralisation of the basicity of the lysine. Any remaining amounts of unreacted material are filtered off, the filtrate is decolorised with charcoal, filtered again and the water is distilled off in a vacuum and at a low temperature or the filtrate is lyophilised. The residue obtained consists of the lysine salt of 2-(4-isobutyl-phenyl)-propionic acid which can be purified, if necessary, by washing with diethyl ether or by crystallisation from 95% ethanol.

EXAMPLE 4

Figure 3:
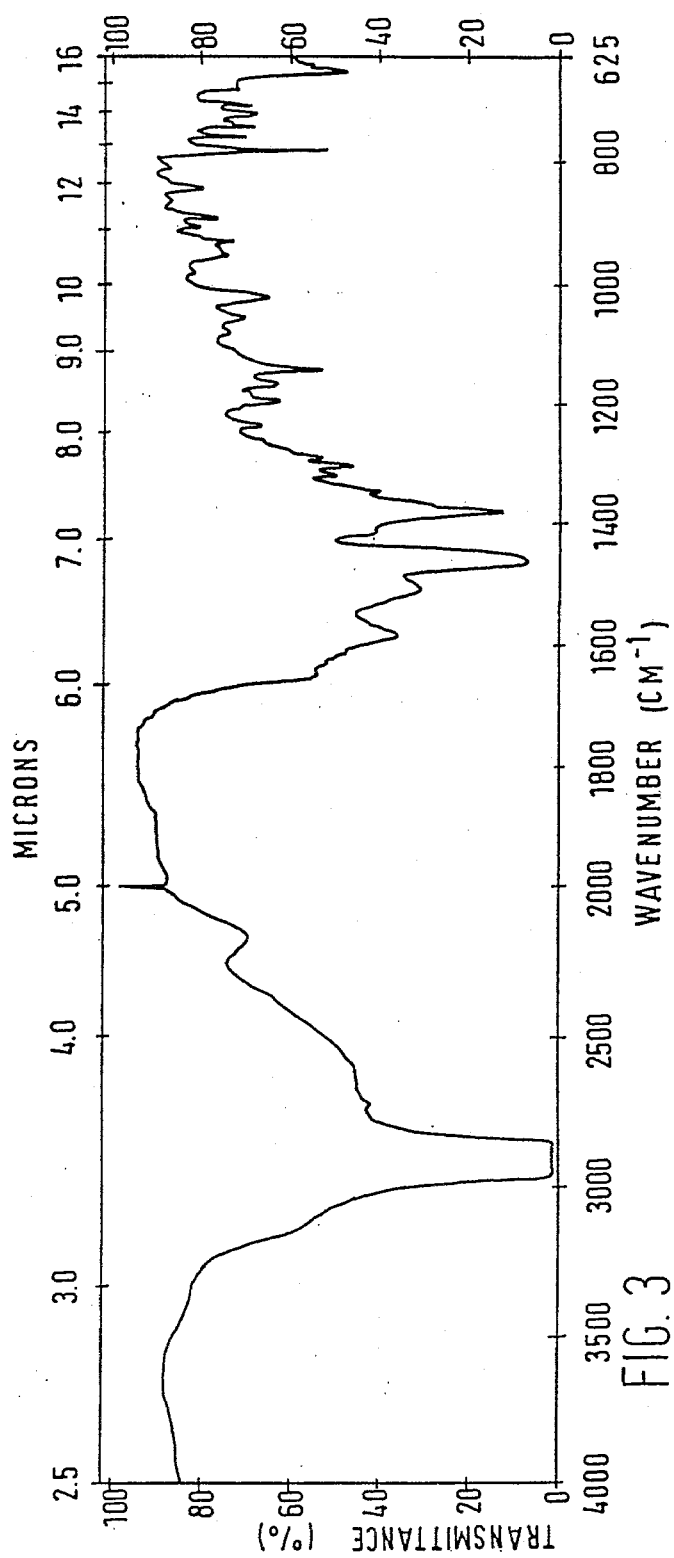

8.7 g. of DL-lysine in the form of a 50% aqueous solution is added dropwise, while stirring, to a solution of 5.8 g. 2-(4-isobutyl-phenyl)-acetic acid in 60 ml. ethanol, followed by dilution of the reaction mixture with 50 ml. isopropanol. A copious precipitate is obtained. After leaving to stand for 2 hours at 4° C., the product is filtered off, washed with a little isopropanol and dried in a vacuum. A good yield of the lysine salt of 2-(4-isobutyl-phenyl)-acetic acid is obtained in the form of a colourless, crystalline solid which is soluble in water; m.p. 184°–186° C. The IR spectrum (see FIG. 3) confirms the structure of the salt.

EXAMPLE 5

By the reaction of 2-(3-benzoyl-phenyl)-propionic acid with a stoichiometric amount of lysine in a manner analogous to that described in Example 1, there is obtained the lysine salt of 2-(3-benzoyl-phenyl)-propionic acid in the form of a water-soluble crystalline solid.

EXAMPLE 6

The reaction of 2-(2,4-dichlorophenoxy)-phenyl-acetic acid with lysine in a manner analogous to that described in Example 1 gives the corresponding lysine salt of 2-(2,4-dichlorophenoxy)-phenyl-acetic acid, which is a water-soluble, colourless, crystalline solid.

EXAMPLE 7

2-(6-Methoxy-β-naphthyl)-propionic acid is reacted with an equimolar amount of D,L-lysine in 50% aqueous solution. Proceeding as in Example 1, there is obtained a high yield of the D,L-lysine salt of 2-(6-methoxy-β-naphthyl)-propionic acid in the form of a colourless, crystalline solid which is soluble in water.

EXAMPLE 8

16 g. 2-(4-isobutyl-phenyl)-propionic acid are dissolved in a mixture of 100 ml. acetone and 30 ml. water and a saturated aqueous solution containing 13.5 g. D,L-arginine is then added thereto dropwise, while stirring. The reaction mixture is further stirred for 1 hour at ambient temperature and then a further 200 ml. acetone are added, whereafter stirring is continued for an hour. The precipitate obtained is then filtered off and washed repeatedly with acetone, again filtered and dried in a vacuum. 17 g. of the D,L-arginine salt of 2-(4-isobutylphenyl)-propionic acid are obtained in the form of a colourless, crystalline solid which melts at 174°–176° C. Analysis and the infra-red spectrum (see FIG. 2 of the accompanying drawings) confirm the structure of the compound. This salt is moderately soluble in water to give a stable solution with a pH close to neutrality.

EXAMPLE 9

Reaction of 2-(4-isobutyl-phenyl)-propionic acid with L-arginine in a manner analogous to that described in Example 8 gives the L-arginine salt of 2-(4-isobutyl-phenyl)-propionic acid, the solubility, stability and pH value in aqueous solution of which are analogous to those of the product obtained in Example 8.

EXAMPLE 10

2-(3-Chloro-4-allyloxyphenyl)-acetic acid is reacted with a stoichiometric amount of arginine in a manner analogous to that described in Example 8 to give the arginine salt of 2-(3-chloro-4-allyloxyphenyl)-acetic acid. The product is a colourless, crystalline salt which is moderately soluble in water.

EXAMPLE 11

Reaction of 2-(4-cyclohexyl-phenyl)-propionic acid with a stoichiometric amount of arginine in a manner analogous to that described in Example 8 gives the arginine salt of 2-(4-cyclohexyl-phenyl)-propionic acid in the form of a colourless, crystalline solid which is moderately soluble in water.

EXAMPLE 12

By the reaction of 2-(3-phenoxy-phenyl)-propionic acid with a stoichiometric amount of arginine in a manner analogous to that described in Example 8, there is obtained the arginine salt of 2-(3-phenoxy-phenyl)-propionic acid in the form of a colourless, crystalline solid which is moderately soluble in water.

EXAMPLE 13

By the reaction of 2-(6-methoxy-β-naphthyl)-propionic acid with the stoichiometric amount of D,L-arginine in a manner analogous to that described in Example 8, there is obtained the D,L-arginine salt of 2-(6-methoxy-β-naphthyl)-propionic acid in the form of a colourless, crystalline solid which is moderately soluble in water.

EXAMPLE 14

By the reaction of 2-(4-isobutyl-phenyl)-acetic acid with the stoichiometric amount of D,L-arginine in a manner analogous to that described in Example 8, there is obtained the D,L-arginine salt of 2-(4-isobutyl-phenyl)-acetic acid in the form of a colourless, crystalline solid. This salt is moderately soluble in water to give a stable solution with a pH close to neutrality.

The method according to the present invention can be carried out with the use of pharmaceutical compositions containing at least one of the salts of general formula (I) in admixture with a solid, liquid or semi-liquid pharmaceutical carrier, which can be administered orally or parenterally.

Solid compositions for oral administration include compressed tablets, pills, dispersible powders and granules. In such solid compositions, one of the new salts is admixed with at least one inert diluent, such as calcium carbonate, starch, alginic acid or lactose. The compositions may also comprise, as is normal practice, additional substances other than inert diluents, for example, lubricating agents, such as magnesium stearate.

Liquid compositions for oral administration include pharmaceutically acceptable emulsions, solutions, suspensions, syrups and elixirs containing inert diluents commonly used in the art, such as water and liquid paraffin. Besides inert diluents, such compositions may also comprise adjuvants, such as wetting and suspension agents, and sweetening and flavouring agents.

Compositions for oral administration include capsules of absorbable material, such as gelatine, containing one of the new salts, with or without the addition of diluents or excipients.

Compositions for parenteral administration include sterile aqueous or non-aqueous solutions, suspensions or emulsions. Examples of non-aqueous solvents or suspending media inclyde propylene glycol, polyethylene glycol, vegetable oils, such as olive oil, and injectable organic esters, such as ethyl oleate. These compositions may also contain adjuvants, such as wetting, emulsifying and dispersing agents. They may be sterilised, for example, by filtration through bacteria-retaining filters, by incorporation into the compositions of sterilising agents, by irradiation or by heating. They may also be produced in the form of sterile solid compositions, which can be dissolved in sterile water or some other sterile injectable medium immediately before use.

The percentage of active material in the compositions which can be used for carrying out the method of the present invention may be varied, it being necessary that it should constitute a proportion such that a suitable dosage for the desired therapeutic effect shall be obtained. In general, the compositions should be administered orally or parenterally to warm-blooded animals, including humans, for producing the desired analgesic and/or anti-inflammatory effects.

In order to demonstrate the usefulness of the method of the present invention for the treatment of humans, a clinical trial has also been carried out using, as active ingredient, the D,L-lysine salt of 2-(4-isobutylphenyl)-propionic acid.

For the clinical trials, the following formulations were used:

| For oral use | |
|---|---|
| each tablet contained: | |
| D,L-lysine salt of 2-(4-isobutyl-phenyl)-propionic acid | 500 mg. |
| starch | 250 mg. |
| magnesium stearate | 25 mg. |
| For parenteral use | |
| each vial contains: | |
| D,L-lysine salt of 2-(4-isobutyl-phenyl)-propionic acid | 500 mg. |
| aqueous ethanol (95%) q.s. ad | 3 ml. |

First, there were ascertained the blood levels of 2-(4-isobutyl-phenyl)-propionic acid obtained after the oral administration of the D,L-lysine salt and these were compared with those obtained with the known sodium 2-(4-isobutyl-phenyl)-propionate, which was also administered orally in tablet form.

For this purpose, 5 healthy adult subjects (A to E) were given a single dose of 500 mg. of the D,L-lysine salt of 2-(4-isobutyl-phenyl)-propionic acid, the dose being administered in the morning on an empty stomach. The blood levels were then determined after 0.5, 1, 1.5, 2, 3, 4 and 5 hours. The following results were obtained for the human blood levels of the D,L-lysine salt of 2-(4-isobutyl-phenyl)-propionic acid, expressed in mcg./ml. of serum, as 2-(4-isobutyl-phenyl)-propionic acid.

TABLE 5

| time (hrs.) | A | B | C | D | E | mean |
|---|---|---|---|---|---|---|
| 0.5 | 24.7 | 30.2 | 24 | 11.5 | 22.8 | 26.9 |
| 1 | 22.3 | 30.5 | 18 | 25.3 | 14.2 | 23.6 |
| 1.5 | 10.5 | 20.1 | 11.3 | 28.8 | 15 | 18.6 |
| 2 | 11.1 | 22.1 | 9 | 21.7 | 25.5 | 17.8 |
| 3 | 11 | 13.9 | 12.8 | 19.4 | 11.1 | 13.1 |
| 4 | 3.4 | 8.9 | 11.2 | 16.4 | 12.4 | 10.2 |
| 5 | 5.5 | 6.4 | 8.6 | 9.2 | 12.3 | 6.3 |

For comparative purposes, 15 days later the same 5 subjects were given an equivalent single dose (300 mg.) of sodium 2-(4-isobutyl-phenyl)-propionate, this also being administered in the morning on an empty stomach, followed by determining the blood levels after the same time intervals as before. The results obtained are given in the following Table 6, the human blood levels of sodium 2-(4-isobutyl-phenyl)-propionate being expressed in mcg./ml. of serum as 2-(4-isobutyl-phenyl)-propionic acid.

TABLE 6

| time (hrs.) | A | B | C | D | E | mean |
|---|---|---|---|---|---|---|
| 0.5 | — | 10.5 | 3.8 | 5.5 | 3.3 | 8.3 |
| 1 | — | 16.6 | 4.5 | 6 | 9.8 | 13.6 |
| 1.5 | — | 11 | 6 | 7 | 8.7 | 11.6 |
| 2 | 0.9 | 10.3 | 8.7 | 16.3 | 7.9 | 12.7 |
| 3 | 1.3 | 3 | 8.7 | 13.6 | 9.6 | 10.8 |
| 4 | 4.2 | 2.7 | 9.6 | 7.3 | 7 | 7.8 |
| 5 | 6.3 | 1.4 | 4.3 | 6.9 | 5.3 | 5.4 |

Comparison of the total mean values of the blood levels of 2-(4-isobutyl-phenyl-propionic acid obtained in the two tests clearly shows that, after the oral administration of the D,L-lysine salt, higher blood levels are always obtained, especially during the first 3 hours, than after the oral administration of the sodium salt.

In a subsequent clinical trial, 33 human subjects were used with an average age of 73.8±6.8, the minimum age being 61 and the maximum age 88; 7 of the subjects were males and the remaining 26 were female.

These subjects presented osteoarticular diseases of a chronic or subacute type, in which, during the period of observation, an evolutive flare-up of a pre-existing mono- or polyarticular arthrosic process was verified, as well as the appearance ex novo of an arthralgic picture with functional impotence of the osteoarticular segments which previously appeared to be undamaged.

Care was taken to avoid using subjects in whom previous treatments with oral anti-inflammatory agents had proved to be badly tolerated at the gastroenteric level, as well as subjects with a relatively accentuated clinical symptomatology.

In these cases, the parenteral route of administration was used so as to obtain, in view of the watersoluble characteristics of the test material, a more rapid symptomatic control. Furthermore, this method of administration permits a ready control of any differences in gastric tolerance as compared with the oral administration route, which is more commonly used.

The most frequently associated pathological states were diabetes mellitus and congestive cardiac insufficiency.

Although the osteoarticular lesions were more or less generalised, the painful and functional symptomatology affected the hip and knee joints in 8 cases, was of a diffuse polyarthrosic type in 17 cases and involved the cervicolumbar area in 5 cases. The remaining subjects presented an arthralgic symptomatology which could not be clearly attributable to precise pathological conditions.

In each case, the conditions of the osteoarticular areas affected were radiographically documented, X-ray examination also being repeated at the end of the treatment.

The treatment consisted of the intramuscular injection of a single dose of 500 mg. of the D,L-lysine salt of 2-(4-isobutyl-phenyl)-propionic acid up to the resolution of the pathological picture, the average duration of treatment being 13.9±3.9 days (minimum 6 days and maximum 20 days).

The test substance was injected in the morning between 8 and 8.30 a.m. Before starting the therapy, midway through it and immediately after it, the following parameters were controlled in order to ascertain how effective the treatment had been: Lansbury's dynamometer (the values of muscular strength were expressed in kg.); the range of articular flexion and extension (the basal finding was expressed conventionally with the notations "+" to "+++," the successive findings being assessed as "unchanged," "increased" or "decreased," compared with the pre-treatment findings; subjective algesic symptomatology, the criteria of evaluation being similar to those adopted for determining the range of articular flexion and extension; finger tip-floor distance test, obtained by measuring the distance between the tips of the fingers and the floor when the subject bends forward; and morning stiffness, this being the time taken for the disappearance of stiffness on awakening.

Thus, for the evaluation of the test substance, it was thus possible to have 3 quantitative parameters (morning stiffness, Lansbury's index and finger tip-floor distance) and 2 semiquantitative parameters (pain symptomatology and flexo-extension strength). This is sufficient to obtain a reliable therapeutic profile in the test subjects, where the subjective element plays a predominant role in determining the clinical picture, as well as the therapeutic response.

The numerical data obtained were analysed statistically by means of the calculation of the Student "t" test on the mean values found before and after treatment.

Particular attention was given to the study of the tolerance of the test material. For this purpose, in addition to a careful annotation of all phenomena of local irritation clearly related to the test material, the following haematochemical indices were also monitored before starting the treatment and immediately after it had finished: erythro-leukocyte count with differentiated morphological evaluation of the leukocytes, blood urea nitrogen, glycaemia, SGOT, SGPT and acid and alkaline phosphatase. A physico-chemical examination of the urine and urinary sediment was also carried out at the same time.

In cases with a history of gastroenteric disorders, even if not drug-dependent, the faeces were tested for the presence of occult blood, using the benzidine test.

All the subjects received the specific therapy warranted by their main disease (diet, hypoglycaemic agents, cardiotonics, antibiotics and the like) but avoiding any administration of steroid or non-steroid anti-inflammatory agents.

In the case of the numerical values regarding the haematochemical examinations, a statistical comparison was made between the basal data and those found immediately after the end of the investigation.

The results regarding the evaluation of the efficacy of the test substance are given in the following Table 7, together with the clinical details of each subject:

TABLE 7 clinical results and local tolerance of lysine isobutylphenyl propionate administered by i.m. route in a single dose (500 mg/day) to 33 patients with degenerative osteoarticular affections

| case no. | age | sex | diagnosis | associated disease | duration treatment (days) | Lansbury test (kg) B | Lansbury test (kg) A | flexo-extension B | flexo-extension A | articular force B | articular force A | fingertip-floor distance (cm) B | fingertip-floor distance (cm) A | pain B | pain A | morning stiffness (mins) B | morning stiffness (mins) A | local tolerance |
|---|---|---|---|---|---|---|---|---|---|---|---|---|---|---|---|---|---|---|
| 1 | 70 | F | polyarthritis | diabetes | 13 | 20 | 20 | + | ++ | unchanged | unchanged | 45 | 45 | ++ | unchanged | 30 | 30 | good |
| 2 | 78 | F | gonarthrosis | cardiac insuff. | 17 | 30 | 30 | ++ | ++ | unchanged | unchanged | 40 | 40 | ++ | reduced | 30 | 10 | good |
| 3 | 79 | F | polyarthrosis | cystopyelitis | 20 | 25 | 25 | ++ | ++ | unchanged | unchanged | 30 | 30 | ++ | reduced | 15 | 0 | good |
| 4 | 70 | F | cervicoarthrosis | myocardiosclerosis | 8 | 25 | 25 | ++ | ++ | unchanged | unchanged | 40 | 30 | ++ | reduced | 15 | 8 | good |
| 5 | 68 | F | spondylarthrosis | diabetes | 15 | 32 | 32 | ++ | ++ | unchanged | unchanged | 30 | 28 | ++ | reduced | 10 | 2 | good |
| 6 | 73 | F | arthrosis rt shoulder | hypertension | 15 | 20 | 20 | ++ | ++ | increased | increased | 35 | 30 | ++ | reduced | 15 | 12 | good |
| 7 | 77 | F | polyarthrosis | obesity | 15 | 30 | 30 | ++ | ++ | unchanged | unchanged | — | — | ++ | reduced | 30 | 0 | good |
| 8 | 86 | M | arthritis rt knee | cardiac insuff. | 17 | — | — | reduced | reduced | increased | increased | — | — | +++ | reduced | — | — | good |
| 9 | 85 | F | cervicoarthrosis | — | 16 | 20 | 20 | reduced | reduced | increased | increased | — | — | ++ | reduced | — | — | good |
| 10 | 63 | F | gonarthrosis | diabetes | 12 | 40 | 40 | ++ | ++ | increased | increased | 15 | 15 | ++ | unchanged | 25 | 25 | good |
| 11 | 73 | M | coxogonarthrosis | obesity | 16 | 35 | incr. | + | + | unchanged | unchanged | 14 | 11 | ++ | reduced | 15 | 10 | good |
| 12 | 88 | F | polyarthrosis | — | 18 | 30 | 30 | ++ | ++ | increased | increased | 45 | 45 | ++ | reduced | 15 | 10 | good |
| 13 | 63 | M | lombar arthrosis | diabetes | 22 | 25 | 25 | ++ | ++ | increased | increased | 9 | 6 | ++ | reduced | 25 | 15 | good |
| 14 | 68 | M | lombosciatalgia | neoplasia | 16 | 25 | 25 | ++ | ++ | unchanged | unchanged | — | — | ++ | reduced | — | — | good |
| 15 | 78 | F | cervicoarthrosis | — | 16 | 30 | 30 | ++ | ++ | unchanged | unchanged | 15 | 15 | ++ | reduced | 10 | 0 | good |
| 16 | 70 | F | arthropathy | diabetes | 16 | 18 | 18 | ++ | ++ | unchanged | unchanged | 30 | 28 | ++ | reduced | 20 | 10 | good |
| 17 | 67 | F | polyarthrosis | diabetes | 16 | 25 | 25 | ++ | ++ | unchanged | unchanged | 45 | 40 | ++ | reduced | 25 | 11 | good |
| 18 | 79 | F | coxoarthrosis | diabetes | 15 | 30 | 30 | ++ | ++ | unchanged | unchanged | 20 | 20 | ++ | reduced | 10 | 5 | good |
| 19 | 65 | F | coxogonarthrosis | cardiac insuff. | 20 | 30 | 30 | ++ | ++ | unchanged | unchanged | 40 | 40 | ++ | reduced | 20 | 10 | good |
| 20 | 75 | F | polyarthrosis | — | 12 | 42 | 42 | + | + | unchanged | unchanged | 45 | 45 | ++ | reduced | 10 | 9 | good |
| 21 | 74 | F | polyarthrosis | — | 12 | 40 | 40 | + | + | increased | increased | 25 | 24 | ++ | unchanged | 25 | 23 | good |
| 22 | 74 | F | left coxoarthrosis | cardiac insuff. | 10 | 35 | 35 | + | + | increased | increased | 40 | 38 | ++ | decreased | 20 | 18 | good |
| 23 | 69 | M | polyarthrosis | — | 9 | 45 | 45 | + | + | unchanged | unchanged | 20 | 18 | ++ | decreased | 25 | 5 | good |
| 24 | 61 | F | polyarthrosis | diabetes | 17 | 48 | 48 | + | + | increased | increased | 50 | 46 | ++ | decreased | 15 | 10 | good |
| 25 | 76 | M | polyarthrosis | — | 8 | 45 | 45 | + | + | unchanged | unchanged | 40 | 35 | ++ | decreased | 20 | 12 | good |
| 26 | 68 | F | polyarthrosis | pyelonephritis | 6 | 20 | 20 | + | + | unchanged | unchanged | — | — | ++ | reduced | — | — | good |
| 27 | 77 | F | polyarthrosis | — | 12 | 45 | 45 | + | + | unchanged | unchanged | — | — | ++ | unchanged | 20 | 18 | good |
| 28 | 72 | F | rt gonarthrosis | — | 15 | 30 | 30 | + | + | increased | increased | — | — | + | unchanged | 20 | 22 | good |
| 29 | 83 | F | polyarthrosis | myocardiosclerosis | 16 | 20 | 20 | + | + | unchanged | unchanged | — | — | ++ | reduced | 25 | 20 | good |
| 30 | 83 | F | arthralgia | atherosclerosis | 10 | 30 | 30 | + | + | increased | increased | — | — | ++ | reduced | 30 | 25 | good |
| 31 | 79 | M | pubic osteolysis | neoplasia | 6 | 30 | 30 | + | + | unchanged | unchanged | — | — | ++ | reduced | 25 | 25 | good |
| 32 | 71 | M | polyarthrosis | diabetes | 12 | 50 | 50 | + | + | increased | increased | 45 | 30 | ++ | reduced | 15 | 10 | good |
| 33 | 75 | F | polyarthrosis | cardiac insuff. | 11 | 30 | 30 | + | + | unchanged | unchanged | — | — | ++ | unchanged | 20 | 20 | good |
| x̄ | 73.8 | | | | 13.9 | 30.96 | | | | | | 33.17 | 30.73 | | | 20.17 | 18.93 | |
| s.d. | ±6.8 | | | | ±3.9 | ±9.19 | | | | | | ±12.4 | ±12.25 | | | ±6.62 | ±8.2 | |
| t | | | | | | | | | | | | 0.9 n.s. | | | | 5.23 (+++) | | |

B = before treatment;
A = after treatment

From an examination of the numerical data and of the results of the statistical analysis, it can be seen that the effect of the treatment was most evident on the morning stiffness; the difference between the pre- and post-treatment duration being highly significant (P<0.01). The data of the Lansbury test are less probative, the pre- and post-treatment mean values being similar. However, in the case of the polyarthrosic patients, the initial values were not too bad and were not such as to constitute a picture of severe articular improvement. Consequently, the test substance appears to have brought about stabilisation, at a safe level, of a situation susceptible to a potential evolutive flare-up in the widest context of a contingent polyarthrosic reactivation. Similar considerations apply to the data for the finger tip-floor distance.

The therapeutic effect of the D,L-lysine salt of 2-(4-isobutyl-phenyl)-propionic acid is most evident on the subjective symptoms: in 27 cases (81.8%), spontaneous pain was reduced following treatment.

The flexo-extension strength showed an increase after administration of the test substance in only 36.3% of the cases but it must be noted that in the 18 cases with major initial involvement of this parameter, 10 patients (55.5%) showed a marked improvement.

The therapeutic efficacy of the test substance can be summarized as follows:
- in 25 patients (case Nos. 2, 3, 4, 5, 6, 7, 8, 11, 12, 13, 15, 16, 17, 18, 19, 20, 21, 22, 23, 24, 25, 29, 30, 31 and 32), the effect observed can be evaluated as "excellent," with significant reduction of the painful and articular symptomatology;
- in 4 patients (case Nos. 9, 10, 14 and 26) a "fair" result was obtained, with reduction of pain and a less evident effect on articular stiffness;
- in another 4 patients (case Nos. 1, 27, 28 and 33), the effect was "poor" or "nil", with no improvement either of the morning stiffness or of the pain.

There were no radiologic changes of the findings observed before starting the investigation. This was to have been expected, bearing in mind the degenerative nature of articular lesions and their poor response to various therapeutic regimens.

The local tolerance of the test substance can be considered as being fully satisfactory.

In no case did the test substance cause pain, either during or immediately after intramuscular injection. Despite several patients being affected with diabetes, no circumscribed or diffused inflammatory infiltrates were ever found in the injection site, even in cases treated for more than 10 days. No local or general allergic phenomena were observed which could be clearly attributed to the test compound.

The statistical analysis of the pre- and post- treatment haematochemical indices (given in detail in Table 8) does not show any significant differences, except for the glycaemic index, this being reduced in comparison with frankly pathologic initial values (P<0.05). This is obviously due to the considerable number of diabetics and to the action of the hypoglaemic therapy which was initiated on admission.

The testing of faeces for occult blood in the pretreatment phase was positive in 14 subjects. At the end of the experiment, the haematic loss was reduced in 6 cases, unchanged in 5 cases, had disappeared in 1 case and had slightly increased in 2 cases. However, the blood counts did not reveal any cases of anaemia which could be considered pathological or at the most suspect.

TABLE 8

| No. of cases | erythrocytes ($\times$ mm$^3$) B | A | No. of cases | leukocytes ($\times$ mm$^3$) B | A | No. of cases | BUN (mg% ml.) B | A | No. of cases | blood sugar (mg% ml.) B | A |
|---|---|---|---|---|---|---|---|---|---|---|---|
| 29 | 4648275 | 4500900 | 29 | 7234 | 6744 | 29 | 20.5 | 21.4 | 27 | 120.1 | 103.1 |
| s.d. | ±474800 | ±414800 | | ±2068 | ±1873 | | ±7.40 | ±15.2 | | ±51.5 | ±29.6 |
| t | 1.78 n.s. | | | 1.33 n.s. | | | 0.4 n.s. | | | 2.10* | |

| No. of cases | alkaline phosphatase (U% ml.) B | A | No. of cases | acid phosphatase (U% ml.) B | A | No. of cases | SGOT (U% ml.) B | A | No. of cases | SGPT (U% ml.) B | A |
|---|---|---|---|---|---|---|---|---|---|---|---|
| 25 | 81.6 | 94.6 | 21 | 9.9 | 9.8 | 29 | 28.9 | 28.06 | 29 | 24.7 | 23.6 |
| s.d. | ±31.5 | ±66.5 | | ±3.3 | ±4.3 | | ±12.2 | ±13.5 | | ±13.2 | ±11.9 |
| t | 0.12 n.s. | | | 0.1 n.s. | | | 0.3 n.s. | | | 0.4 n.s. | |

Study of general tolerance of lysine isobutyl-phenyl propionate administered by i.m. route in a single dose (500 mg./day) to 33 patients with degenerative osteoarticular diseases. Comparison of haematochemical values before (B) and after (A) treatment.

The above results clearly demonstrate that the D,L-lysine salt of 2-(4-isobutyl-phenyl)-propionic acid is safe and clinically effective and that gastroenteric intolerance, such as gastric microhaemorrhage, which occurs when the known compound sodium 2-(4-isobutyl-phenyl)-propionate is administered orally, does not occur.

We claim:

1. A method of relieving pain and treating inflammatory conditions in warm-blooded animals, including humans, which comprises administering to a warm-blooded animal suffering from pain or from an inflammatory condition a phenylalkanoic acid salt of the general formula:

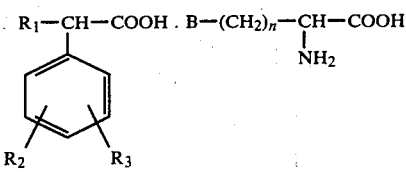

wherein $R_1$ is a hydrogen atom or a methyl radical, $R_2$ is a halogen atom or an alkyl radical containing up to 5 carbon atoms, which may be straight-chained or branched, or is a cycloalkyl radical or is a phenoxy or benzoyl radical, which may be substituted by one or two halogen atoms, $R_3$ is a hydrogen atom or an allyloxy radical, B is a primary, secondary or tertiary amino group or a guanidino or amidino group and n is a whole number not greater than 5, said salt being administered in an amount sufficient to relieve pain or to ameliorate an inflammation condition.

2. A method according to claim 1, wherein the salt is the D,L-lysine salt of 2-(4-isobutyl-phenyl)-propionic acid.

3. A method according to claim 1, wherein the salt is the L-lysine salt of 2-(4-isobutyl-phenyl)-propionic acid.

4. A method according to claim 1, wherein the salt is the lysine salt of 2-(4-isobutyl-phenyl)-acetic acid.

5. A method according to claim 1, wherein the salt is the lysine salt of 2-(3-benzoyl-phenyl)-propionic acid.

6. A method according to claim 1, wherein the salt is the lysine salt of 2-(2,4-dichlorophenoxy)-phenyl-acetic acid.

7. A method according to claim 1, wherein the salt is the D,L-arginine salt of 2-(4-isobutyl-phenyl)-propionic acid.

8. A method according to claim 1, wherein the salt is the L-arginine salt of 2-(4-isobutyl-phenyl)-propionic acid.

9. A method according to claim 1, wherein the salt is the arginine salt of 2-(3-chloro-4-allyloxyphenyl)-acetic acid.

10. A method according to claim 1, wherein the salt is the arginine salt of 2-(4-cyclohexyl-phenyl)-propionic acid.

11. A method according to claim 1, wherein the salt is the arginine salt of 2-(3-phenoxy-phenyl)-propionic acid.

12. A method according to claim 1, wherein the salt is the D,L-arginine salt of 2-(6-methoxy-$\beta$-naphthyl)-propionic acid.

13. A method according to claim 1, wherein the salt is the D,L-arginine salt of 2-(4-isobutyl-phenyl)-acetic acid.

14. A method according to claim 1, wherein the salt is used in admixture with a solid, liquid or semi-liquid pharmaceutical diluent or carrier.

* * * * *